United States Patent [19]
Matsuyama et al.

[11] Patent Number: 5,429,935
[45] Date of Patent: * Jul. 4, 1995

[54] PROCESS FOR THE PRODUCTION OF OPTICALLY ACTIVE 2-HYDROXY-4-PHENYL-3-BUTENOIC ACID

[75] Inventors: Akinobu Matsuyama, Niigata; Ichiro Takase; Yoichiro Ueda, both of Hyogo; Yoshinori Kobayashi, Niigata, all of Japan

[73] Assignee: Daicel Chemical Industries, Ltd., Osaka, Japan

[*] Notice: The portion of the term of this patent subsequent to Mar. 16, 2010 has been disclaimed.

[21] Appl. No.: 102,230

[22] Filed: Aug. 5, 1993

Related U.S. Application Data

[60] Continuation-in-part of Ser. No. 885,974, May 20, 1992, which is a division of Ser. No. 459,787, Mar. 1, 1990, Pat. No. 5,194,380.

[30] Foreign Application Priority Data

Jul. 12, 1988 [JP] Japan .................. 63-173469
Jul. 12, 1988 [JP] Japan .................. 63-173470
Oct. 7, 1988 [JP] Japan .................. 63-253020

[51] Int. Cl.$^6$ ............................ C12P 7/42
[52] U.S. Cl. ...................... 435/146; 435/280; 435/822; 435/824; 435/830; 435/836; 435/840; 435/843; 435/850; 435/852; 435/853; 435/857; 435/873; 435/874; 435/885; 435/911; 435/921; 435/931
[58] Field of Search ............... 435/146, 280, 822, 824, 435/830, 836, 840, 843, 850, 852, 853, 857, 873, 874, 885, 911, 921, 930

[56] References Cited

U.S. PATENT DOCUMENTS 5,194,380  3/1993  Matsuyama et al. ............... 435/146

FOREIGN PATENT DOCUMENTS 6187640  10/1984  Japan .

OTHER PUBLICATIONS

Nerdel et al (1956) Chem. Ber., 89:671–677.

Primary Examiner—Herbert J. Lilling
Attorney, Agent, or Firm—Birch, Stewart, Kolasch & Birch

[57] ABSTRACT

Optically active 2-hydroxy-4-phenyl-3-butenoic acid can be obtained by treating 2-oxo-4-phenyl-3-butenoic acid with an optionally treated microorganism capable of asymmetrically reducing the 2-oxo-4-phenyl-3-butenoic acid into (R)-2-hydroxy-4-phenyl-3-butenoic acid or (S)-2-hydroxy-4-phenyl-3-butenoic acid to thereby asymmetrically reduce the same into (R)-2-hydroxy-4-phenyl-3-butenoic acid or (s) -2-hydroxy-4-phenyl-3-butenoic acid.

12 Claims, No Drawings

PROCESS FOR THE PRODUCTION OF OPTICALLY ACTIVE 2-HYDROXY-4-PHENYL-3-BUTENOIC ACID

This application is a continuation-in-part of application Ser. No. 07/885,974 filed on May 20, 1992 which is a divisional of application Ser. No. 07/459,787 filed on Mar. 1, 1990, now U.S. Pat. No. 5,194,380 the entire contents of which are hereby incorporated by reference.

BACKGROUND OF THE INVENTION

This invention relates to a process for the production of optically active 2-hydroxy-4-phenyl-3-butenoic acid. More particularly, it relates to a process for the production of optically active 2-hydroxy-4-phenyl-3-butenoic acid which comprises treating 2-oxo-4-phenyl-3-butenoic acid with an optionally treated microorganism capable of asymmetrically reducing the 2-oxo-4-phenyl-3-butenoic acid into (R)-2-hydroxy-4-phenyl-3-butenoic acid or (S)-2-hydroxy-4-phenyl-3-butenoic acid and collecting the (R)-2-hydroxy-4-phenyl-3-butenoic acid or (S)-2-hydroxy-4-phenyl-3-butenoic acid thus formed.

Optically active 2-hydroxy-4-phenyl-3-butenoic acid is an important intermediate in the production of various drugs, optically active and physiologically active substances and derivatives thereof.

Further, optically active 2-hydroxy-4-phenylbutyric acid, which is an important intermediate in the production of drugs such as ACE inhibitors, can be readily obtained by bringing optically active 2-hydroxy-4-phenyl-3-butenoic acid into contact with a hydrogenation catalyst such as palladium in a hydrogen atmosphere.

Known methods for the production of optically active 2-hydroxy-4-phenyl-3-butenoic acid include one which comprises treating a racemic mixture of said acid with bornylamine to thereby form diastereomers and then optically resolving the same [cf. Chem. Ber., 89, 671–677 (1956)] and another one comprising optical resolution through liquid chromatography with the use of a packing comprising a carrier containing a metal salt of an optically active amino acid bound thereto (cf. Japanese Patent Laid-Open No. 87640/1986). However, the former method requires a complicated procedure, which makes it undesirable from the industrial viewpoint. On the other hand, the latter method is disadvantageous from the economic viewpoint. Thus it has been demanded to develop a simple and economical method for producing optically active 2-hydroxy-4-phenyl-3-butenoic acid. In addition, there has been known no process for the production of optically active 2-hydroxy-4-phenyl-3-butenoic acid from 2-oxo-4-phenyl-3-butenoic acid by using a microorganism capable of asymmetrically reducing the 2-oxo-4-phenyl-3-butenoic acid.

SUMMARY OF THE INVENTION

The present inventors have developed a process for producing an optically active 2-hydroxy-4-phenyl-3-butenoic acid based upon reduction of the 2-keto-4-phenyl-3-butenoic acid starting material by a microorganism. Accordingly, it is one object of the invention to provide a method for producing optically active 2-hydroxy-4-phenyl-3-butenoic acid having a high enantiomeric purity. The method is composed in part of culture of a microorganism in a medium containing 2-keto-4-phenyl-3-butenoic acid as a starting material.

It is a further object of the invention to provide a method of enzymatically reducing 2-keto-4-phenyl-3-butenoic acid to an optically active 2-hydroxy homolog. The enzyme used for this process can be either a crude enzyme preparation derived from a microorganism, or alternatively, a highly purified enzyme preparation can be used.

The present inventors have noticed asymmetric reduction with a microorganism as a process for readily producing optically active 2-hydroxy-4-phenyl-3-butenoic acid of a high optical purity and attempted to search for microorganisms suitable for this purpose. As a result, they have found out that a microorganism belonging to the genus *Lactobacillus, Leuconostoc, Streptococcus, Sporolactobacillus, Pediococcus, Arthrobacter, Agrobacterium, Ambrosiozyma, Achromobacter, Arthroascus, Aureobacterium, Bacillus, Botryoascus, Brevibacterium, Candida, Clavispora, Corynebacterium, Flavobacterium, Geotrichum, Hansenula, Kluyveromyces, Lipomyces, Lodderomyces, Proteus, Pseudomonas, Saccharomycopsis, Schizosaccharomyces, Stephanoascus, Torulaspora, Trigonopsis, Wickerhamiella, Enterobacter, Klebsiella* and *Xanthomonas* can asymmetrically reduce 2-oxo-4-phenyl-3-butenoic acid to thereby give (R)-2-hydroxy-4-phenyl-3-butenoic acid and that a microorganism belonging to the genus *Lactobacillus, Leuconostoc* or *Streptococcus* can asymmetrically reduce 2-oxo-4-phenyl-3-butenoic acid to thereby give (S)-2-hydroxy-4-phenyl-3-butenoic acid. Furthermore, the cells can be washed and resuspended prior to use in the process of the present invention. Alternatively, the cells can be lyophilized or treated with acetone or lysed with distilled water. Acetone treatment or lysis with distilled water provides a crude enzyme preparation due to disruption of the cell membranes. An enzyme which reduces the 2-oxo compound to its 2-hydroxy equivalent can also be purified from the microorganism.

Any of the whole cells or preparations described above can be immobilized by known methods for use in the process of the present invention.

DETAILED DESCRIPTION OF THE INVENTION

In the present invention, therefore, any microorganism belonging to the genus *Lactobacillus, Leuconostoc, Streptococcus, Sporolactobacillus, Pediococcus, Arthrobacter, Agrobacterium, Ambros iozyma, Achromobacter, Arthroascus, Aureobacterium, Bacillus, Botryoascus, Brevibacterium, Candida, Clavispora, Corynebacterium, Flavobacterium, Geotrichum, Hansenula, Kluyveromyces, Lipomyces, Lodderomyces, Proteus, Pseudomonas, Saccharomycopsis, Schizosaccharomyces, Stephanoascus, Torulaspora, Trigonopsis, Wickerhamiella, Enterobacter, Klebsiella* or *Xanthomonas* and capable of asymmetrically reducing 2-oxo-4-phenyl-3-butenoic acid to thereby give (R)-2-hydroxy-4-phenyl-3-butenoic acid or any one belonging to the genus *Lactobacillus, Leuconostoc* or *Streptococcus* and capable of asymmetrically reducing 2-oxo-4-phenyl-3-butenoic acid to thereby give (S)-2-hydroxy-4-phenyl-3-butenoic acid can be used.

Particular examples of the microorganism capable of producing (R)-2-hydroxy-4-phenyl-3-butenoic acid from 2-oxo-4-phenyl-3-butenoic acid include *Lactobacillus lactis* AHU 1059, *Streptococcus faecalis* IFO 12964, *Leuconostoc mesenteroides* subsp. *dextranicum* IFO 3349, *Pediococcus acidilactici* NRIC 1102, *Sporolactobacillus inulinus* NRIC 1133, *Arthrobacter citreus* IAM 12341,

*Agrobacterium radiobacter* IFO 12664, *Ambrosiozyma cicatricosa* IFO 1846, *Ambrosiozyma platypodis* IFO 1471, *Achromobacter pestifer* ATCC 23584, *Arthroascus javanensis* IFO 1848, *Aureobacterium testaceum* IFO 12675, *Bacillus licheniformis* IFO 12200, *Botryoascus synnaedendrus* IFO 1604, *Brevibacterium iodinum* IFO 3558, *Candida parapsilosis* IFO 1396, *Candida rugosa* IFO 0750, *Clavispora lusitaniae* IFO 1019, *Corynebacterium glutanicum* ATCC 13032, *Flavobacterium suaveolens* IFO 3752, *Geotrichum candidum* IFO 4601, *Hansenula fabianii* IFO 1253, *KlUyveromyces lactis* IFO 1903, *Lipomyces starkeyi* IFO 1289, *Lodderomyces elongisporus* IFO 1676, *Proteus vulgaris* IFO 3167, *Pseudomonas aureofaciens* IFO 3522, *Saccharomycopsis lipolytica* IFO 1550, *Saccharomycopsis fibuligera* IFO 0103, *Schizosaccharomyces octosporus* IFO 0353, *Stephanoascus ciferrii* IFO 1854, *Torulaspora delbrueckii* IFO 0381, *Trigonopsis variabillis* IFO 0755, *Wickerhamiella domercquii* IFO 1857, *Enterobacter aerogenes* AHU 1338, *Klebsiella pneumonias* IAM 1063 and *Xanthomonas oryzae* IAM 1657.

On the other hand, examples of the microorganism capable of producing (S)-2-hydroxy-4-phenyl-3-butenoic acid from 2-oxo-4-phenyl-3-butenoic acid include *Lactobacillus plantrum* IFO 3070, *Streptococcus lactis* NRIC 1149 and *Leuconostoc mesenteroides* AHU 1416.

These microorganisms may be either wild strains, variants or recombinants obtained through genetic engineering techniques such as cell fusion or gene manipulation.

The microorganisms having IFO numbers assigned thereto are described in the List of Cultures, 8th ed., vol. 1 (1988) published by the Institute for Fermentation Osaka (IFO) and are available therefrom. Those having AHU numbers are described in the Catalogue of Cultures, 4th ed. (1987) published by Japan Federation of Culture Collection (JFCC) and are available from the Faculty of Agriculture, Hokkaido University. Further, those having ATCC numbers are described in the Catalogue of Bacteria Phages RDNA Vectors, 16th ed. (1985) published by American Type Culture Collection (ATCC) and are available therefrom. Those having NRIC numbers are described in the Culture Collection of NODAI No. 1 (1985) published by Tokyo University of Agriculture and are available therefrom. Those having IAM numbers are available form the Institute of Applied Microbiology, the University of Tokyo.

In order to culture the microorganism to be used in the present invention, any medium may be used without restriction, so long as said microorganism can grow therein. For example, any carbon source available for said microorganism may be used. Examples thereof include sugars such as glucose, fructose, sucrose and dextrin; alcohols such as sorbitol, ethanol and glycerol; organic acids such as fumaric acid, citric acid, acetic acid and propionic acid and salts thereof; hydrocarbons such as paraffin: and mixtures thereof. Examples of a nitrogen source include ammonium salts of inorganic acids, such as ammonium chloride, ammonium sulfate and ammonium phosphate; ammonium salts of organic acids, such as ammonium fumarate and ammonium citrate; organic or inorganic nitrogen-containing compounds such as meat extract, yeast extract, corn steep liquor, casein hydrolyzate and urea; and mixtures thereof. The medium may further contain appropriate nutritional sources commonly employed in culturing microorganisms, for example, inorganic salts, trace metal salts and vitamins. Furthermore, a growth promoter for the microorganism, a factor capable of elevating the productivity of the target compound of the present invention or a substance effective in maintaining the pH value of the medium at a desired level may be added thereto.

The culture may be conducted at a pH value of from 3.5 to 9.5, preferably from 4 to 8, at a temperature of from 20° to 45° C., preferably from 25° to 37° C., under aerobic or anaerobic conditions suitable for each microorganism for from 5 to 120 hours, preferably from 12 to 72 hours.

The reduction may be conducted by using the culture medium as such. Alternately, the cells may be separated by, for example, centrifuging, and optionally washed. Then the cells are resuspended in a buffer solution or water and 2-oxo-4-phenyl-3-butenoic acid is added to the suspension thus obtained and reacted therewith. In this reaction, it is sometimes preferable to add a carbon source such as glucose or sucrose to thereby supply energy. The cells may be used as such in the form of viable cells. Alternately, they may be those which have been ground, treated with acetone or lyophilized. These optionally treated cells may be immobilized prior to the use by a conventional method, for example, the polyacrylamide gel method, the sulfur-containing polysaccharide gel method (the carrageenan gel method), the alginic acid gel method or the agar gel method. Furthermore, an enzyme obtained from said treated cells by combining known methods may be used therefor. One method for purifying an enzyme which reduces 2-oxo-4-phenyl-3-butenoic acid to the corresponding 2-hydroxy compound is described below. The purified enzyme may be immobilized in a similar manner as for the whole cells.

The 2-oxo-4-phenyl-3-butenoic acid may be used as such. Alternately, it may be dissolved in water or an inert organic solvent or dispersed in a surfactant. It may be added either at once at the initiation of the reaction or in portions. The 2-oxo-4-phenyl-3-butenoic acid may be used in the form of various salts such as ammonium, sodium, calcium or potassium salt.

The reaction may be conducted at a pH value of from 3 to 9, preferably from 5 to 8, at from 10° to 60° C., preferably from 20° to 40° C., for from 1 to 120 hours with or without stirring. It is preferable that the concentration of the substrate ranges from 0.1 to 10%, though the concentration of substrate is not restricted to that range.

The optically active 2-hydroxy-4-phenyl-3-butenoic acid thus formed may be collected directly from the reaction mixture or after separating the cells. It may be extracted with an organic solvent and then purified by a common method such as column chromatography or recrystallization.

According to the process of the present invention for the production of optically active 2-hydroxy-4-phenyl-3-butenoic acid by using a microorganism, optically active 2-hydroxy-4-phenyl-3-butenoic acid of a high optical purity can be readily produced. Thus it is highly advantageous as an industrial process.

EXAMPLES

To further illustrate the present invention, and not by way of limitation, the following Examples are presented.

In the following Examples, the absolute configuration and optical purity of a reaction product were determined by extracting the reaction product with ethyl acetate and subjecting the product to high-performance liquid chromatography with the use of an optical resolution column Ecolumn: Chiral-pack WH (mfd. by Daicel Chemical Industries, Ltd., packed with silica gel containing copper salt of L-proline bound thereto), 4.6 mm (i.d.) ×250 mm, solvent: 0.5 mM CuSO$_4$ (aqueous) /acetonitrile =4:1, flow rate: 1.5 ml/min, detection: at 254 nm. The reaction yield was determined by high-performance liquid chromatography with the use of a reverse-phase column [column: Nucleosil 1OC18, 4.6 mm (i.d.) ×250 mm, solvent: 40 mM potassium phosphate solution (pH 3.0)/acetonitrile =4:1, flow rate: 1 ml/min, detection: spectroscopic at 254 nm.

EXAMPLE 1

A medium comprising 2% glucose, 1% yeast extract, 1% peptone, 10 ppm MnSO$_4$ and 1% calcium carbonate was used for lactic acid bacteria. A medium comprising 1% glucose, 0.5% yeast extract, 0.5% peptone, 0.5% meat extract and 0.5% NaCl (pH 7) was used for other bacteria. A medium comprising 2% glucose, 0.3% yeast extract, 0.5% peptone and 0.3% malt extract (pH 6) was used for yeasts. 100 ml of each medium was introduced into a 500-ml Erlenmeyer flask and sterilized. Then one platinum loopful of each strain listed in Table 1 was inoculated into the corresponding medium and subjected to rotary shaking culture for 48 hours. After completion of the culture, the cells were separated by centrifuging and washed with a physiological saline solution once to thereby give viable cells. 50 ml of distilled water was introduced into a 500-ml Erlenmeyer flask and the above-mentioned viable cells were suspended therein. After adding 5 g of sucrose and 0.5 g of calcium carbonate thereto, the mixture was shaken at 30° C. for 10 minutes. Then 0.5 g of potassium 2-keto-4-phenyl-3-butenoate was added thereto and the mixture was allowed to react under shaking at 30° C. for 40 hours. After the completion of the reaction, the pH value of the reaction mixture was adjusted to 1 or below with sulfuric acid. Then it was extracted with 100 mi of ethyl acetate and the solvent was removed from the extract. Then the amount and optical purity of the (R)-2-hydroxy-4-phenyl-3-butenoic acid thus formed were determined by high-performance liquid chromatography.

Table 1 summarizes the results.

TABLE 1

| Strain | Yield of (R)-2-hydroxy-4-phenyl-3-butenoic acid (%) | Optical purity of (R)-2-hydroxy-4-phenyl-3-butenoic acid (% e.e.) |
| --- | --- | --- |
| Lactobacillus lactis AHU 1059 | 11 | 67 |
| Streptococcus faecalis IFO 12964 | 14 | 62 |
| Leuconostoc mesenteroides subsp. dextranicum IFO 3349 | 92 | 100 |
| Pediococcus acidilactici NRIC 1102 | 10 | 100 |
| Sporolactobacillus inulinus NRIC 1133 | 16 | 68 |
| Lactobacillus lactis ATCC 12315 | 16 | 100 |
| Lactobacillus Viridescens ATCC 12706 | 14 | 46 |
| Leuconostoc dextranicum ATCC 17072 | 96 | 100 |
| Leuconostoc mesenteroides AHU 1067 | 93 | 100 |
| Arthrobacter citreus IAM 12341 | 20 | 100 |
| Agrobacterium radiobacter IFO 12664 | 13 | 100 |
| Ambrosiozyma cicatricosa IFO 1846 | 11 | 100 |
| Ambrosiozyma platypodis IFO 1471 | 10 | 100 |
| Achromobacter pestifer ATCC 23584 | 15 | 100 |
| Arthroascus javanensis IFO 1848 | 12 | 32 |
| Aureobacterium testaceum IFP 12675 | 12 | 20 |
| Bacillus licheniformis IFO 12200 | 10 | 100 |
| Botryoascus synnaedendrus IFO 1604 | 13 | 100 |
| Brevibacterium iodinum IFO 3558 | 15 | 100 |
| Candida parapsilosis IFO 1396 | 19 | 100 |
| Saccharomycopsis lipolytica IFO 1550 | 12 | 100 |
| Saccharomycopsis fibuligera IFO 0103 | 13 | 100 |
| Schizosaccharomyces octosporus IFO 0353 | 10 | 100 |
| Stephanoascus ciferrii IFO 1854 | 19 | 100 |
| Torulaspora delbrueckii IFO 0381 | 14 | 100 |
| Trigonopsis variabillis IFO 0755 | 15 | 100 |
| Wickerhamiella domercquii IFO 1857 | 11 | 95 |
| Enterobacter aerogenes AHU 1338 | 13 | 94 |
| Klebsiella pneumoniae IAM 1063 | 12 | 70 |
| Xanthomonas oryzae AIM 1657 | 11 | 100 |
| Lactobacillus plantrum IFO 3070 | 24 | 99 |
| Streptococcus lactis NRIC 1149 | 32 | 49 |
| Leuconostoc mesenteroides AHU 1416 | 14 | 100 |
| Candida rugosa IFO 0750 | 17 | 100 |
| Clavispora lusitaniae IFO 1019 | 16 | 100 |
| Corynebacterium glutamicum ATCC 13032 | 11 | 93 |
| Flavobacterium suaveolens IFO 3752 | 11 | 70 |
| Geotrichum candidum IFO 4601 | 19 | 100 |
| Hansenula fabianii IFO 1253 | 13 | 100 |
| Kluyveromyces lactis IFO 1903 | 14 | 100 |
| Lipomyces starkeyi IFO 1289 | 10 | 83 |
| Lodderomyces elongisporus IFO 1676 | 14 | 100 |
| Proteus vulgaris IFO 3167 | 10 | 100 |
| Pseudomonas aureotaciens IFO 3522 | 11 | 100 |

EXAMPLE 2

2 L of the same medium as that used in Example 1 contained in 5 L jar fermenter was inoculated with

*Leuconostoc mesenteroides* subsp. dextranicum IFO 3349. The strain was cultured at 30° C. under stirring at 100 rpm for 40 hours. After completion of the culture, the cells were collected by centrifuging and washed with 1 L of water. Then these cells were suspended in 500 ml of water, and 5 g of potassium 2-keto-4-phenyl-3-butenoate, 50 g of glucose and 4 g of calcium carbonate were added thereto. The obtained mixture was allowed to react at 30° C. under stirring for 48 hours and then the pH value thereof was adjusted to 1 or below with sulfuric acid. Then it was extracted twice with an equal volume of ethyl acetate. The ethyl acetate phase was dehydrated over anhydrous Glauber's salt and the solvent was removed therefrom under reduced pressure. Thus 4.0 g of 2-hydroxy-4-phenyl-3-butenoic acid was obtained in the form of crude crystals. By recrystallizing from ethanol, 3.8 g of crystals of (R)-2-hydroxy-4-phenyl-3-butenoic acid were obtained (optical purity: 100% e.e., yield: 93%).

EXAMPLE 3

An enzyme which will reduce 2-oxo-4-phenyl-3-butenoic acid to form (R)- or (S)-2-hydroxy-4-phenyl-3-butenoic acid can be purified from the microorganisms listed in Table 1. The enzyme was purified as follows.

The cells are sonicated and the supernatant obtained by centrifugation is brought to 80% saturation by adding solid ammonium sulfate. The precipitate is harvested by centrifugation, dissolved in 20 mM phosphate buffer (pH 8.0) and dialyzed against the same buffer. The clear supernatant obtained by centrifugation is put on a column of DEAE-Toyopearl 650M (Toso Co., Ltd.) and eluted with the same buffer. The main activity fractions are then dialyzed against buffer, and then applied to a column of HF-Toyopearl 55F (Toso Co., Ltd.) and eluted with the same buffer. The main activity fractions are concentrated.

What is claimed is:

1. A process for the production of optically active 2-hydroxy-4-phenyl-3-butenoic acid which comprises:
   (i) treating 2-oxo-4-phenyl-3-butenoic acid with whole cells of a microorganism capable of asymmetrically reducing the 2-oxo-4-phenyl-3-butenoic acid into (R)-2-hydroxy-4-phenyl-3-butenoic acid or (S)-2-hydroxy-4-phenyl-3-butenoic acid to thereby asymmetrically reduce the same into (R)-2-hydroxy-4-phenyl-3-butenoic acid or (S)-2-hydroxy-4-phenyl-3-butenoic acid, and
   (ii) recovering said (R)-2-hydroxy-4-phenyl-3-butenoic acid or (S)-2-hydroxy-4-phenyl-3-butenoic acid.

2. A process as claimed in claim 1, wherein said microorganism capable of asymmetrically reducing 2-oxo-4-phenyl-3-butenoic acid into (R)-2-hydroxy4-phenyl-3-butenoic acid is selected from the group consisting of the genera *Lactobacillus Leuconostoc, Streptococcus, Sporolactobacillus, Pediococcus, Arthrobacter, Agrobacterium, Ambrosiozyma, Achromobacter, Arthroascus, Aureobacterium, Bacillus, Botryoascus, Brevibacterium, Candida, Clavispora, Corynebacterium, Flavobacterium, Geotrichum, Hansenula, Kluyveromyces, Lipomyces, Lodderomyces, Proteus, Pseudomonas, Saccharomycopsis, Schizosaccharomyces, Stephanoascus, Torulaspora, Trigonopsis, Wickerhamiella, Enterobacter, Klebsiella* and *Xanthomonas*.

3. A process as claimed in claim 1 wherein said microorganism capable of asymmetrically reducing 2-oxo-4-phenyl-3-butenoic acid into (S)-2-hydroxy-4-phenyl-3-butenoic acid is selected from the group consisting of the genera *Lactobacillus, Leuconostoc* and *Streptococcus*.

4. The process of claim 1, wherein said whole cells of microorganism are treated by a treatment selected from the group consisting of washing, lyophilizing, suspension in acetone and suspension in distilled water, prior to treating said 2-oxo-4-phenyl-3-butenoic acid.

5. A method of producing optically active 2-hydroxy-4-phenyl-3-butenoic acid which comprises:
   (i) purifying an enzyme which can reduce 2-oxo-4-phenyl-3-butenoic acid to form (S)-2-hydroxy-4-phenyl-3-butenoic acid or (R)-2-hydroxy-4-phenyl-3-butenoic acid;
   (ii) contacting said enzyme with a solution containing said 2-oxo-4-phenyl-3-butenoic acid; and
   (iii) recovering said (S)-2-hydroxy-4-phenyl-3-butenoic acid or said (R)-2-hydroxy-4-phenyl-3-butenoic acid thus formed;
   wherein said enzyme is purified from an organism of a genus selected from the group consisting of *Lactobacillus, Leuconostoc, Streptococcus, Sporolactobacillus, Pediococcus, Arthrobacter, Agrobacterium, Ambrosiozyma, Achromobacter, Arthroascus, Aureobacterium, Bacillus, Botryoascus, Brevibacterium, Candida, Clavispora, Corynebacterium, Flavobacterium, Geotrichum, Hansenula, Kluyveromyces, Lipomyces, Lodderomyces, Proteus, Pseudomonas, Saccharomycopsis, Schizosaccharomyces, Stephanoascus, Torulaspora, Trigonopsis, Wickerhamiella, Enterobacter, Klebsiella* and *Xanthomonas*;
   wherein the enzyme purifying step (i) is performed by a method comprising:
   (a) sonicating the cells and obtaining a supernatant therefrom;
   (b) adding ammonium sulfate to 80% saturation to form a precipitate;
   (c) collecting the precipitate from step (b).

6. The method of claim 5, wherein said enzyme purifying step further comprises:
   (d) dissolving the precipitate in a phosphate buffer;
   (e) dialyzing the dissolved precipitate against said phosphate buffer to obtain a dialysate;
   (f) applying the dialysate to a DEAE chromatography column; and
   (g) eluting the enzyme from said DEAE column with said phosphate buffer and collected the resulting DEAE eluate.

7. The method of claim 6, wherein said enzyme purifying step further comprises:
   (h) dialyzing said DEAE eluate against said phosphate buffer to obtain a second dialysate;
   (i) applying said second dialysate to an HF-Toyopearl 55F chromatography column;
   (j) eluting the enzyme from said HF-Toyopearl 55F with said phosphate buffer and collecting said HF-Toyopearl 55F eluate.

8. The method of claim 7, wherein the enzyme purifying step (i) is performed by a method comprising:
   (a) sonicating the cells and obtaining a supernatant therefrom;
   (b) adding ammonium sulkate to 80% saturation to form a precipitate;
   (c) collecting the precipitate from step (b).

9. The method of claim 8, wherein said enzyme purifying step further comprises:
   (d) dissolving the precipitate in a phosphate buffer;
   (e) dialyzing the dissolved precipitate against said phosphate buffer to obtain a dialysate;

(f) applying the dialysate to a DEAE chromatography column; and (g) eluting the enzyme from said DEAE column with said phosphate buffer and collected the resulting DEAE eluate.

10. The method of claim 9, wherein said enzyme purifying step further comprises:

(h) dialyzing said DEAE eluate against said phosphate buffer to obtain a second dialysate;

(i) applying said dialysate to an HF-Toyopearl 55F chromotography column;

(j) eluting the enzyme from said HF-Toyopearl 55F with said phosphate buffer and collecting said HF-Toyopearl 55F eluate.

11. The method of claim 5, wherein said enzyme forms (S)-2-hydroxy-4-phenyl-3-butenoic acid and is purified from an organism of a genus selected from the group consisting of *Lactobacillus, Leuconostoc* and *Streptococcus.*

12. The method of claim 5, wherein said enzyme is immobilized.

* * * * *